United States Patent
Brown et al.

(10) Patent No.: US 10,662,462 B2
(45) Date of Patent: May 26, 2020

(54) METHODS AND COMPOSITIONS FOR DETECTING THERAPEUTIC NUCLEIC ACIDS

(71) Applicant: Biogen MA Inc., Cambridge, MA (US)

(72) Inventors: Kirk M. Brown, Swampscott, MA (US); Denitza Raitcheva, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 15/550,576

(22) PCT Filed: Feb. 11, 2016

(86) PCT No.: PCT/US2016/017558
§ 371 (c)(1),
(2) Date: Aug. 11, 2017

(87) PCT Pub. No.: WO2016/130811
PCT Pub. Date: Aug. 18, 2016

(65) Prior Publication Data
US 2018/0037939 A1 Feb. 8, 2018

Related U.S. Application Data

(60) Provisional application No. 62/115,102, filed on Feb. 11, 2015.

(51) Int. Cl.
C07H 21/02 (2006.01)
C07H 21/04 (2006.01)
C12Q 1/6816 (2018.01)

(52) U.S. Cl.
CPC ..... *C12Q 1/6816* (2013.01); *C12Q 2521/327* (2013.01); *C12Q 2537/161* (2013.01); *C12Q 2561/101* (2013.01)

(58) Field of Classification Search
CPC .......................... A61K 31/713; C12N 15/115
See application file for complete search history.

(56) References Cited

U.S. PATENT DOCUMENTS

| 2004/0005618 A1 | 1/2004 | Yu et al. |
| 2010/0062436 A1 | 3/2010 | Jarosch et al. |

| 2013/0210655 A1 | 8/2013 | Chong et al. | |
| 2013/0231261 A1* | 9/2013 | Ozinsky | C12Q 1/6823 506/9 |
| 2013/0336986 A1* | 12/2013 | Falcenberg | C12N 15/1137 424/158.1 |

FOREIGN PATENT DOCUMENTS

| JP | 4905959 B2 | 3/2012 |
| WO | WO 2014/165814 A1 | 10/2014 |
| WO | WO 2014/189628 A1 | 11/2014 |

OTHER PUBLICATIONS

PCT/US2016/017558, Jan. 3, 2017, International Search Report and Written Opinion.
PCT/US2016/017558, Aug. 24, 2017, International Preliminary Report on Patentability.
International Search Report and Written Opinion for Application No. PCT/US2016/017558 dated Jan. 3, 2017.
International Preliminary Report on Patentability for Application No. PCT/US2016/017558 dated Aug. 24, 2017.
De Serres et al., Development of a Novel Scintillation Proximity Competitive Hybridization Assay for the Determination of Phosphorothioate Antisense Oligonucleotide Plasma Concentrations in a Toxicokinetic Study. Anal Biochem. Jan. 15, 1996;233(2):228-233.
Goodrich et al., Direct Detection of Genomic DNA by Enzymatically Amplified SPR Imaging Measurements of RNA Microarrays. J Am Chem Soc. Apr. 7, 2004;126(13):4086-4087.
Ho et al., Potent antisense oligonucleotides to the human multidrug resistance-1 mRNA are rationally selected by mapping RNA-accessible sites with oligonucleotide libraries. Nucleic Acids Research. May 15, 1996;24(10):1901-1907.
Macrae et al., In Vitro reconstitution of the human RISC-loading complex. Proc Natl Acad Sci U S A. Jan. 15, 2008;105(2):512-517.

* cited by examiner

*Primary Examiner* — Amy H Bowman
(74) *Attorney, Agent, or Firm* — Wolf, Greenfield & Sacks, P.C.

(57) ABSTRACT

The present disclosure relates, in some aspects, to the field of nucleic acid detection. Disclosed herein are methods and compositions for detecting nucleic acids using synthetic single-stranded ribonucleic acids (RNAs). In certain embodiments, synthetic single-stranded RNAs are used to detect therapeutic nucleic acids, such as therapeutic deoxyribonucleic acids (DNAs) and/or therapeutic ribonucleic acids (RNAs).

19 Claims, 5 Drawing Sheets
Specification includes a Sequence Listing.

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
tgcctttagg attctagaca                                            20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: Modified with 2'O-Methyl-modified RNA
<220> FEATURE:
<221> NAME/KEY: misc_feature
<222> LOCATION: (17)..(20)
<223> OTHER INFORMATION: Modified with 2'O-Methyl-modified RNA

<400> SEQUENCE: 2
ugcctttagg attctagaca                                            20

<210> SEQ ID NO 3
<211> LENGTH: 108
<212> TYPE: RNA
<213> ORGANISM: Artificial Sequence
<220> FEATURE:
<223> OTHER INFORMATION: Synthetic Polynucleotide

<400> SEQUENCE: 3
ggaguugucc caauucuugu ugaauuagau ggugaugucu agaauccuaa aggcacuguc   60
aguggagagg gugaagguga ugcaacauac ggaaaacuua cccuuaaa             108

<210> SEQ ID NO 4
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 4
attgctgacc                                                        10

<210> SEQ ID NO 5
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 5
ggtcagcaat                                                        10
```

METHODS AND COMPOSITIONS FOR DETECTING THERAPEUTIC NUCLEIC ACIDS

RELATED APPLICATION

This application is a national stage filing under 35 U.S.C. § 371 of PCT International Application PCT/US2016/017558, filed Feb. 11, 2016 entitled "METHODS AND COMPOSITIONS FOR DETECTING ANTISENSE OLIGONUCLEOTIDE THERAPEUTICS," which claims the benefit under 35 U.S.C. § 119(e) of U.S. provisional application No. 62/115,102, filed Feb. 11, 2015, the contents of each of which are incorporated by reference herein in their entirety.

FIELD OF THE INVENTION

The present disclosure relates, in some aspects, to the field of nucleic acid detection.

BACKGROUND OF INVENTION

Therapeutic biologically-active nucleic acids (e.g., antisense oligonucleotides and RNA interference (RNAi) agents) can be delivered in vivo to target cells and tissues. Following delivery of such therapeutic nucleic acids, it is often difficult to determine whether and how much of the nucleic acids reached the intended target, particularly because the extent of nucleic-acid uptake by the target cells and tissues varies. As a result, determining an effective dose of a therapeutic nucleic acid can be challenging.

SUMMARY OF INVENTION

The present disclosure provides, in some aspects, robust and quantitative methods and compositions for detecting nucleic acids of interest (e.g., therapeutic nucleic acids) obtained from or present in a biological sample using a synthetic single-stranded ribonucleic acid (synthetic ssRNA). In some aspects, the presence and/or amount of a nucleic acid of interest in a sample (e.g., in a biological sample) is determined by evaluating the ability of the nucleic acid of interest to bind to a synthetic ssRNA that is added to the sample. In some embodiments, the ability of a therapeutic nucleic acid to bind to a synthetic ssRNA is evaluated by detecting the degradation of synthetic ssRNA bound to the therapeutic nucleic acid. In some embodiments, a synthetic ssRNA includes a region complementary to a region of a nucleic acid of interest and, thus, is capable of binding specifically to the nucleic acid. For simplicity and clarity, a nucleic acid of interest to which a synthetic ssRNA is designed to bind is referred to herein as a "therapeutic nucleic acid." It should be understood, however, that the synthetic ssRNAs of the present disclosure may be designed to bind to any nucleic acid of interest. The present disclosure is not limited to therapeutic nucleic acids. Thus, in some embodiments, a synthetic ssRNA of the present disclosure is designed to bind to nucleic acids (e.g., synthetic nucleic acids) that are used to regulate cellular and/or biological processes (e.g., metabolic processes) in non-therapeutic contexts (e.g., nucleic acids used in manufacturing, engineering, mining, environmental, or other applications).

Typically, a therapeutic nucleic acid is delivered to a subject, and a biological sample from the subject is later obtained to determine whether the therapeutic nucleic acid is present in the sample, whether it is capable of binding to its intended target and, in some embodiments, to quantitate the therapeutic nucleic acid. In some embodiments, cleavage of a synthetic ssRNA can be detected (e.g., indirectly) by detecting a reduction in the amount of the synthetic ssRNA (e.g., by using an amplification reaction to determine the amount of the synthetic ssRNA). Factors impacting the relative amount of ssRNA include, without limitation, the concentration of the ssRNA in the reaction, the amount of therapeutic nucleic acid present in the sample, the amount of RNase H in the reaction, and the time of the reaction. In some embodiments, for example, with the use of therapeutic RNAi reagents, the cleavage of the ssRNA may be dependent on the amount of RNAi reagent that is unwound and activated into the RISC complex, because intact double-stranded therapeutic RNAi reagents would unlikely be active in this assay. The amount of cleaved ssRNA typically depends on the amount of ssRNA and other reagents that are added to the sample. In some embodiments, the amounts and reaction conditions are calibrated such that most or all of the ssRNA is cleaved if the "therapeutic nucleic acid" is present. In some embodiments, less than 100% of the ssRNA is cleaved. In some embodiments, it may be important to compare the amount of ssRNA remaining in a sample following cleave to an expected amount in order to detect the presence of cleavage, as the cleaved products are not being detected directly but rather their presence is being inferred from the disappearance of the ssRNA.

As an example, for detection of a therapeutic deoxyribonucleic acid (DNA), a synthetic ssRNA may be added to a biological sample together with RNase H enzyme. If the therapeutic DNA is present in the sample, the synthetic ssRNA will bind to a single strand of the therapeutic DNA to form a double-stranded region. RNase H catalyzes cleavage of the synthetic ssRNA bound to the single-stranded therapeutic DNA. Detection of a change in the level of synthetic ssRNA, as compared to a control (e.g., no therapeutic nucleic acid control or placebo control), for example, via an amplification reaction, is indicative of the presence and function of the therapeutic DNA in the biological sample (e.g., whether the therapeutic DNA is capable of binding to its intended target). As another example, for the detection of a therapeutic RNA, a synthetic ssRNA may be added to the biological sample and will work together with components of the RNA-induced silencing complex (RISC) present in (e.g., endogenous to) the sample. If the therapeutic RNA is present in the sample, the synthetic ssRNA will bind to a single strand of the therapeutic RNA to form a double-stranded region. Without being bound by theory, this is likely because RISC binds to the single-stranded RNA, and guides it to the complementary region of the synthetic ssRNA. When the single-stranded therapeutic RNA is bound to its complementary region on the synthetic ssRNA, an Argonaute protein, present as a component of RISC, is activated, which catalyzes the cleavage of the ssRNA bound to the single-stranded therapeutic RNA. Detection of a cleaved synthetic RNA is indicative of the presence and function of the therapeutic RNA in the biological sample (e.g., whether the therapeutic RNA is capable of binding to its intended target).

The present disclosure is based, at least in part, on results showing that a synthetic ssRNA of the present disclosure is capable of detecting the level of a DNA antisense (SEQ ID NO: 1). In some embodiments, a synthetic ssRNA of the present disclosure is used to detect the level of a short-interfering RNA (siRNA).

Some aspects of the present disclosure provide methods of detecting a therapeutic nucleic acid, the methods comprising (a) contacting a therapeutic nucleic acid with (i) a synthetic single-stranded ribonucleic acid (ssRNA) that is longer than and contains a region that is complementary to the therapeutic nucleic acid under conditions that permit nucleic acid hybridization, and (ii) an enzyme that binds to double-stranded nucleic acid and is capable of mediating cleavage of the synthetic ssRNA, thereby forming a first reaction mixture, and (b) performing at least one assay to detect cleavage of the synthetic ssRNA.

Some aspects of the disclosure provide compositions comprising: (a) a therapeutic nucleic acid, (b) a synthetic single-stranded ribonucleic acid (ssRNA) that is longer than and contains a region that is complementary to the therapeutic nucleic acid; and (c) RNase H.

In some embodiments, a therapeutic nucleic acid is obtained from a biological sample. The biological sample, in some embodiments, is obtained from a subject (e.g., a human subject).

In some embodiments, a therapeutic nucleic acid is administered (e.g., intravenously) to the subject.

In some embodiments, a therapeutic nucleic acid is DNA. A therapeutic nucleic acid, in some embodiments, is single-stranded DNA. A single-stranded therapeutic DNA, in some embodiments, is antisense oligonucleotide (ASO).

In some embodiments, the enzyme is RNase H. The enzyme, in some embodiments, is endogenous to the biological sample.

In some embodiments, an assay to detect cleavage of a synthetic ssRNA comprises performing a reverse transcription reaction using at least a portion of the first reaction mixture and a primer that is complementary to and binds specifically to the synthetic ssRNA (e.g., to the forward primer-binding region and/or the reverse primer-binding region), thereby producing a second reaction mixture. In some embodiments, the step of performing at least one assay to detect cleavage of the synthetic ssRNA further comprises performing a nucleic acid amplification reaction using at least a portion of the second reaction mixture and a pair of primers that are complementary to and bind specifically to a complementary DNA (cDNA) produced by the reverse transcription reaction, and wherein amplification of a nucleic acid indicates that the enzyme did not cleave the synthetic ssRNA.

In some embodiments, a nucleic acid amplification reaction is a quantitative polymerase chain reaction (qPCR). The amplification reaction, in some embodiments, is performed in the presence of a blocker for determining the level of the therapeutic nucleic acid.

Some aspects of the disclosure provide methods of detecting a therapeutic deoxyribonucleic acid DNA, the methods comprising (a) contacting the therapeutic DNA with (i) a synthetic ssRNA that is longer than and contains a region that is complementary to the therapeutic DNA under conditions that permit nucleic acid hybridization, and (ii) RNase H, and (b) performing at least one assay to detect RNase H-mediated cleavage of the synthetic ssRNA.

Some aspects of the present disclosure provide methods of detecting a therapeutic ribonucleic acid (RNA) (e.g., RNAi interference (RNAi) agent) by (a) contacting a biological sample containing therapeutic RNA with a synthetic ssRNA that is longer than and contains a region that is complementary to a nucleic acid strand of the therapeutic RNA, wherein the biological sample comprises an RNA-induced silencing complex containing an Argonaute protein (or variant thereof); and (b) performing at least one assay to detect cleavage of the synthetic ssRNA.

Some aspects of the present disclosure provide compositions comprising (a) therapeutic RNA (e.g., an RNAi agent), (b) synthetic ssRNA that is longer than and contains a region that is complementary to the therapeutic RNA, and (c) an RNA-induced silencing complex containing an Argonaute protein (or variant thereof).

In some embodiments, a biological sample is obtained from a subject (e.g., a human subject).

In some embodiments, a therapeutic RNA is administered to a subject. A therapeutic RNA, in some embodiments, is an RNAi agent. In some embodiments, an RNAi agent is a short-hairpin RNA (shRNA), short-interfering RNA (siRNA), a micro RNA (miRNA), or a miRNA inhibitor.

In some embodiments, an RNA-induced silencing complex is endogenous to the biological sample.

In some embodiments, an assay used to detect cleavage of the synthetic ssRNA comprises performing a reverse transcription reaction using at least a portion of the first reaction mixture and a primer that is complementary to and binds specifically to the synthetic ssRNA, thereby producing a second reaction mixture.

In some embodiments, an assay used to detect cleavage of the synthetic ssRNA further comprises performing a nucleic acid amplification reaction using at least a portion of the second reaction mixture and a pair of primers that are complementary to and bind specifically to a cDNA produced by the reverse transcription reaction, and wherein amplification of a nucleic acid indicates that the Argonaute protein did not cleave the synthetic ssRNA.

In some embodiments, the primer that is used for reverse transcription is complementary to a region of the ssRNA that is outside of the therapeutic-binding region of the synthetic ssRNA (e.g., a 3' region of the ssRNA).

In some embodiments, the primers used to amplify the cDNA are respectively complementary to complementary strands of the cDNA in the regions flanking, or otherwise outside of, the therapeutic-binding region.

In some embodiments, a nucleic acid amplification reaction is a quantitative polymerase chain reaction (qPCR). The amplification reaction, in some embodiments, is performed in the presence of a blocker for determining the level of the RNAi agent.

DETAILED DESCRIPTION OF INVENTION

Figure 1:
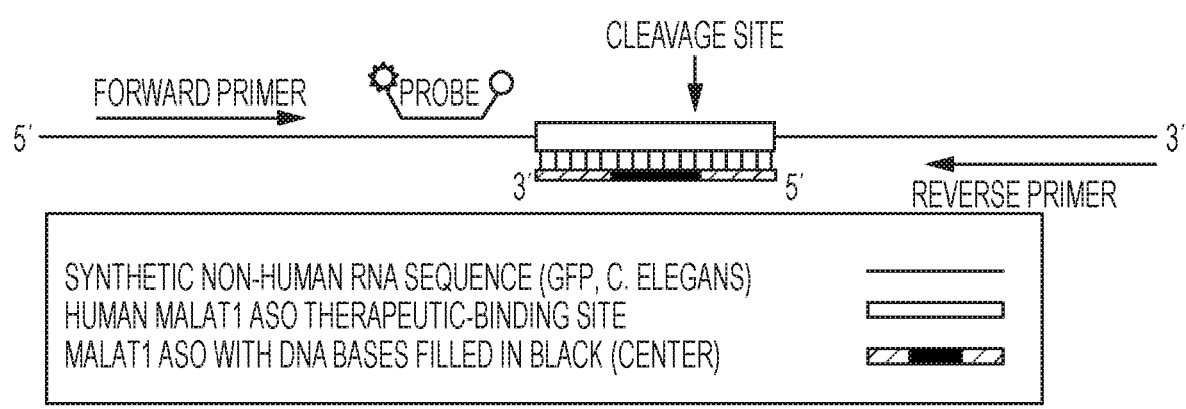
FIG. 1 shows a schematic of a non-limiting example of a synthetic single-stranded RNA (ssRNA) of the present disclosure bound to a therapeutic nucleic acid, specifically a DNA antisense oligonucleotide (ASO). The synthetic ssRNA is designed to contain a region that is complementary to the therapeutic nucleic acid (referred to herein as a "therapeutic-binding site"), forward and reverse primer-binding sites flanking the therapeutic-binding site, and a probe-binding site. The synthetic RNA molecule can be cleaved by RNase H (indicated by the arrow) when bound to the therapeutic nucleic acid. Also shown is a non-limiting example of a probe, such as a qPCR probe, which may have a fluorophore (shown as circle on the left side of the probe) and a quencher (shown as circle on the right side of the probe).

Evaluating the efficacy of a therapeutic nucleic acid, in some aspects, includes determining (1) whether the therapeutic nucleic acid has reached and is capable of binding to nucleic acids of interest present in cells and/or tissues and (2) the level of the therapeutic nucleic acid present in target cells and/or tissues. Following in vivo delivery of therapeutic nucleic acids, they are often compartmentalized into lysosomes within the cells and remain inactive and, thus, are difficult to evaluate by conventional means. The methods and compositions provided herein may be used to detect and, in some instances, quantify in biological samples therapeutic nucleic acids, such as, for example, therapeutic DNA and/or therapeutic RNA. This is achieved, in some aspects, by evaluating the ability of the therapeutic nucleic acid to bind to a synthetic ssRNA that is added to a sample containing the therapeutic nucleic acid.

Synthetic single-stranded ribonucleic acids (ssRNAs) of the present disclosure are designed to contain a "therapeutic-binding region" that is complementary to a region (or the entire length) of a therapeutic nucleic acid of interest (e.g., a DNA antisense oligonucleotide or an RNA interference (RNAi) agent). Thus, in the presence of a therapeutic nucleic acid of interest, a synthetic ssRNA binds specifically to the therapeutic nucleic acid.

Synthetic Single-Stranded RNA (ssRNA)

Methods for detecting a nucleic acid of interest are performed, in some embodiments, by contacting the nucleic acid with a synthetic ssRNA that is longer than and contains a region that is complementary to (and thus binds to) the therapeutic nucleic acid. A "synthetic" ssRNA is a ssRNA that does not occur in nature. A synthetic ssRNA refers to a molecule that is chemically, or by other means, synthesized. Synthetic ssRNAs of the present disclosure include those that are chemically modified, or otherwise modified, but can base pair with naturally-occurring or other synthetic nucleic acids. It should be understood that while a synthetic ssRNA as a whole is not naturally-occurring, it may include nucleotide sequences that occur in nature.

A region that is complementary to (and thus binds to) a therapeutic nucleic acid is herein referred to as a "therapeutic-binding region." In some embodiments, the therapeutic binding region is complementary to and binds to a portion of the therapeutic nucleic acid. In some embodiments, the therapeutic binding region is complementary to and binds the full length of the therapeutic nucleic acid. Nucleic acid binding, also referred to as "hybridization," refers to hydrogen bonding, also known as Watson-Crick base pairing, between complementary bases of nucleic acids. Examples of complementary bases include guanine and cytosine, which form three hydrogen bonds with each other, and adenine and thymine, which form two hydrogen bonds with each other.

Two nucleic acids or nucleic acid regions are "complementary" to one another if they base-pair with each other to form a double-stranded nucleic acid. Two nucleic acid regions are "perfectly complementary" to one another if every nucleotide of one nucleic acid region can base-pair with every nucleotide of the other nucleic acid region. For example, a region of a ssRNA having the sequence 5'-ATTGCTGACC-3' (SEQ ID NO: 4) is perfectly complementary to a region of a therapeutic nucleic acid having the sequence 5'-GGTCAGCAAT-3' (SEQ ID NO: 5). A therapeutic-binding region need not be perfectly complementary to the full length of a therapeutic nucleic acid or a region of a therapeutic nucleic acid in order to form a double-stranded nucleic acid. In some embodiments, the therapeutic-binding region of a synthetic ssRNA and a therapeutic nucleic acid are 50% to 100% complementary. In some embodiments, the therapeutic-binding region of a synthetic ssRNA and a therapeutic nucleic acid are 60% to 100%, 70% to 100%, 80% to 100%, 85% to 100%, 90% to 100%, 95% to 100%, 98% to 100%, or 99% to 100% complementary. In some embodiments, a therapeutic-binding region of a synthetic ssRNA is perfectly (i.e., 100%) complementary to the therapeutic nucleic acid to which it is designed to bind. In some embodiments, a therapeutic-binding region of a synthetic RNA and a therapeutic nucleic acid of interest are sufficiently complementary to permit binding to each other while avoiding non-specific binding of the synthetic ssRNA to nucleic acid sequences that are not of interest.

Synthetic ssRNAs of the present disclosure are typically longer than a therapeutic nucleic acid to which they are designed to specifically bind and, in some embodiments, contain at each end a primer-binding region (e.g., a forward primer-binding region and a reverse primer-binding region). In some embodiments, a synthetic ssRNA further comprises a probe-binding region. A non-limiting example of a synthetic ssRNA of the present disclosure is depicted in FIG. 1, which shows a therapeutic-binding region (already bound to a complementary therapeutic nucleic acid) flanked by forward primer-binding region, a reverse primer-binding region, and a probe-binding region. The length of a synthetic ssRNA may vary. Nucleotide length is measured by the number of individual nucleotides in a single-stranded nucleic acid. In some embodiments, a synthetic ssRNA is at least one nucleotide (nt) longer than the therapeutic nucleic acid to which it is designed to bind. In some embodiments, a synthetic ssRNA is at least 5 nucleotides (nt) longer than the therapeutic nucleic acid to which it is designed to bind. In some embodiments, a synthetic ssRNA is at least 10 nucleotides, at least 15 nucleotides, at least 20 nucleotides, at least 25 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, or at least 500 nucleotides longer than the therapeutic nucleic acid to which it is designed to bind.

In some embodiments, a synthetic ssRNA is at least 5% longer than the therapeutic nucleic acid to which it is designed to bind. In some embodiments, a synthetic ssRNA is at least 10%, at least 15%, at least 20%, at least 25%, at least 30%, at least 40%, at least 50%, at least 60%, at least 70%, at least 80%, at least 90%, at least 100%, at least 125%, at least 150%, at least 175%, at least 200%, at least 250%, at least 300%, at least 350%, at least 400%, at least 450%, or at least 500% longer than the therapeutic nucleic acid to which it is designed to bind. In some embodiments, a synthetic ssRNA is at least 600%, 700%, 800%, 900% or 1000% longer than the therapeutic nucleic acid to which it is designed to bind.

In some embodiments, binding of a synthetic ssRNA to a therapeutic nucleic acid forms a partially double-stranded molecule, wherein each end of the synthetic ssRNA is single-stranded. That is, in some embodiments, a therapeutic nucleic acid binds to a central region of a synthetic ssRNA such that the ssRNA has a 3' and a 5' single-stranded overhang, as shown, for example, in FIG. 1. In some embodiments, a therapeutic nucleic acid binds to an end region (e.g., the 5' end) of a synthetic ssRNA such that the ssRNA has only one single-stranded overhang (e.g., a 3' overhang). For example, after binding to a therapeutic nucleic acid, a synthetic ssRNA may have a 3' overhang that can be used for reverse transcription and/or amplification (e.g., in a linear amplification assay).

A "forward primer-binding region" may be located at the 5' end of a synthetic ssRNA, while a "reverse primer-binding region" may be located at the 3' end of a synthetic ssRNA. Respectively complementary forward and reverse primers may be used in an amplification reaction (e.g., a polymerase chain reaction (PCR)) with the synthetic ssRNA to determine whether the synthetic ssRNA in a sample is bound to a therapeutic nucleic acid. In some embodiments, a forward primer-binding region and/or a reverse primer-binding region have a length of at least 5 nucleotides. In some embodiments, a forward primer-binding region and/or a reverse primer-binding region have a length of at least 10 nucleotides, at least 15 nucleotides, at least 20 nucleotides, at least 25 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, or at least 500 nucleotides.

In some embodiments, a synthetic ssRNA contains a "probe-binding region" designed to bind a complementary nucleic acid probe (e.g., a hydrolysis probe) that is detectably labeled. This is particularly useful for methods of the present disclosure that include a quantification step. For example, a TaqMan® probe is a hydrolysis probe that has a FAM™ or VICO dye label on the 5' end, and minor groove binder (MGB) non-fluorescent quencher (NFQ) on the 3' end. The TaqMan® probe principle relies on the 5'-3' exonuclease activity of Taq® polymerase to cleave the dual-labeled TaqMan® probe during hybridization to a complementary probe-binding region and fluorophore-based detection. TaqMan® probes increase the specificity of detection in quantitative measurements of an accumulated amplified synthetic ssRNA during the exponential stages of a quantitative PCR reaction.

A probe-binding region, in some embodiments, is located at the 5' end of a synthetic ssRNA. In some embodiments, a probe-binding region is located at the 3' end of a synthetic ssRNA. In some embodiments, a probe-binding region is located between a forward primer-binding region and a therapeutic-binding region of a synthetic ssRNA. In some embodiments, a probe-binding region is located between a reverse primer-binding region and a therapeutic-binding region of a synthetic ssRNA. In some embodiments, a probe-binding region has a length of at least 5 nucleotides. In some embodiments, a probe-binding region has a length of at least 10 nucleotides, at least 15 nucleotides, at least 20 nucleotides, at least 25 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, or at least 500 nucleotides.

Synthetic ssRNA of the present disclosure, in some embodiments, are synthesized in vitro. Methods for synthesizing nucleic acids, including automated nucleic acid synthesis, are known.

Synthetic ssRNAs of the present disclosure may be designed to bind specifically to therapeutic nucleic acids of interest. Nucleic acids are polymeric macromolecules comprising a plurality of nucleotides. In some embodiments, the nucleotides are deoxyribonucleotides or ribonucleotides. In some embodiments, nucleotides are selected from the group consisting of adenine, guanine, cytosine, thymine, uracil and inosine. In some embodiments, nucleotides are modified nucleotides. In some embodiments, a nucleotide modification includes a 5' cap structure.

Detecting Therapeutic Deoxyribonucleic Acid (DNA)

Aspects of the present disclosure are directed to methods of detecting, assessing the function of, and/or quantitating DNA of interest (e.g., therapeutic DNA). In some embodiments, the methods comprise (a) contacting a therapeutic DNA with (i) a synthetic single-stranded ribonucleic acid (ssRNA) that is longer than (e.g., contains a flanking region on one or both sides of the region that is complementary to the therapeutic nucleic acid) and contains a region that is complementary to the therapeutic DNA under conditions that permit nucleic acid hybridization, and (ii) an enzyme that binds to double-stranded nucleic acid and is capable of mediating cleavage of the synthetic ssRNA, thereby forming a first reaction mixture, and (b) performing at least one assay to detect cleavage of the synthetic ssRNA. In the presence of a functional therapeutic DNA, the synthetic ssRNA and the therapeutic DNA bind to form an RNA-DNA duplex.

In some embodiments, the enzyme is an RNase H family member (e.g., RNase H1 and RNase H2), or a variant thereof. RNase H is a non-specific endonuclease and catalyzes the cleavage of the RNA component of an RNA-DNA duplex via a hydrolytic mechanism (see, e.g., Cerritelli S. M. et al. FEBS J. 2009 March; 276(6): 1494-505, incorporated by reference herein). The ribonuclease activity of RNase H results in cleavage of the 3'-O—P bond of RNA in a DNA/RNA duplex to produce 3'-hydroxyl and 5'-phosphate terminated products. RNase H will not cleave DNA or unhybridized (or single-stranded) RNA. Thus, in the presence of an RNA-DNA duplex, RNase H cleaves the synthetic ssRNA. Detection of a change in the synthetic ssRNA RNA (e.g., resulting from cleavage of the synthetic ssRNA) is indicative is indicative of the presence of a functional therapeutic DNA in the sample, and detection of intact (e.g., uncleaved) synthetic ssRNA is indicative of the absence of a functional therapeutic DNA in the sample.

In some embodiments, the enzyme that binds to double-stranded nucleic acid and is capable of mediating cleavage of the synthetic ssRNA is added to sample (or reaction mixture) containing the therapeutic DNA of interest. In some embodiments, the enzyme is endogenous to the sample (e.g., the biological sample) containing the therapeutic DNA of interest.

In some embodiments, a therapeutic DNA is an antisense oligonucleotide (ASO). DNA ASOs are short, synthetic single-stranded nucleic acids, typically 4 to 30 nucleotides in length, and are complementary to and bind to a target nucleic acid of interest (e.g., a target allele of interest). Upon binding, the ASOs can alter the original function of the RNA (e.g., a messenger RNA (mRNA)) through an array of different mechanisms (see, e.g., DeVos S. L. et al. *Neurotherapeutics,* 2013, July; 10(3):486-97). Other therapeutic DNAs are contemplated herein.

In some embodiments, the level (also referred to as the quantity) of therapeutic DNA is determined by determining the level of cleaved synthetic ssRNA. In some embodiments, the level of therapeutic DNA is determined by PCR (e.g., quantitative PCR). In some embodiments, the level of therapeutic DNA is determined by 5' RACE or 3'RACE. Other amplification methods may be used as provided herein. In some embodiments, the level of therapeutic DNA is determined by other suitable methods, which include without limitation Northern blot analysis.

The length of a therapeutic DNA (e.g., DNA ASO) may vary. In some embodiments, a therapeutic DNA has a length of 4 nucleotides to 500 nucleotides, 4 nucleotides to 250 nucleotides, 4 nucleotides to 100 nucleotides, or 4 nucleotides to 50 nucleotides. In some embodiments a therapeutic DNA has a length of at least 5 nucleotides. In some embodiments, a therapeutic DNA has a length of at least 10 nucleotides, at least 15 nucleotides, at least 20 nucleotides, at least 25 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, or at least 500 nucleotides.

Therapeutic DNAs of the present disclosure may be naturally-occurring or synthetic. In some embodiments, therapeutic DNAs contain at least one modification, including a DNA backbone or sugar modification. Typically, modifications to a therapeutic DNA are made to enhance its stability, pharmacokinetic and/or therapeutic properties. Methods of modifying nucleic acids generally, including DNA (e.g., DNA ASOs) are known in the art and may be used as provided herein (see, e.g., DeVos S. L. et al., *Neurotherapeutics,* 2013, July; 10(3):486-97; and Dias N. et al. *Mol. Cancer Thera.,* 2002, March; 1(5): 347-55, the contents of each which are incorporated herein by reference). Non-limiting examples of nucleotide modifications include phosphorothioate backbone modifications, 2'-O-methyl group sugar modifications and/or the substitution of non-naturally occurring nucleotide bases.

In some embodiments, at least one modification is a phosphorothioate (PS) backbone modification. A PS modification is a well-known and widely used modification for antisense oligonucleotide (ASO) therapeutics. The non-bridging phosphate oxygen atoms in natural DNAs are replaced with sulfur atoms, equipping ASOs with properties that support their use as a systemically delivered therapeutic. The PS backbone modification may increase the stability of the ASO against nuclease degradation, to facilitate the PS-modified ASO reaching its target RNA in cells and tissues. Further, PS-modified ASOs can recruit the enzyme RNase H to promote cleavage of the target RNA. In some embodiments, the PS-modified ASO recruits the enzyme RNase H to cleave a synthetic ssRNA.

In some embodiments, at least one modification is a thiophosphoramidate (TP) backbone modification. A TP-modification abrogates any RNaseH activity, rendering the backbone more suited for non-degrading RNA manipulations, including alternative splicing changes, translation inhibition, and microRNA hindrance. ASO backbones may be modified, in some embodiments, by replacing the sugar phosphate backbone with an isostere, such as with a morpholino ASO. It should be appreciated that the entire ASO backbone need not be modified. For example, modifications may be made to a portion of an ASO, such as one or more ends of an ASO with a region of unmodified DNA.

In some embodiments, at least one modification is in a DNA sugar moiety. In some embodiments, a therapeutic DNA is modified at the 2'-position of the sugar moiety. Modifications at a 2' position can enhance ASO potency by facilitating target binding. In some embodiments, a 2'-modification is a 2'-O-methyl modification. In some embodiments a 2'-modification is a 2'-O-methoxyethyl sugar modification. A 2'-sugar modifications, as provided herein, may increase resistance to nucleases and may also reduce nonspecific protein binding, which can, in turn, reduce a DNA ASO toxicity profile.

In some embodiments, a therapeutic DNA comprises at least one "locked nucleic acid (LNA)." The ribose moiety of a LNA nucleotide is modified with an extra bridge connecting the 2' oxygen and 4' carbon. The bridge "locks" the ribose in the 3'-endo (North) conformation, which increases the hybridization properties of oligonucleotides. In some embodiments, LNA ASOs demonstrate increased potency, improved activity and/or toxicity profiles. Additional 2'-sugar modifications are known in the art and include but are not limited to, a 2'-fluoro additive. While the 2'-sugar modifications, provided herein, may enhance binding to the mRNA target, they may also reduce or even completely obstruct RNase H from cleaving the target RNA. One modification used to circumvent this limitation has been to adopt the "gapmer" design, whereby regions of 2'-modified residues flank a longer central unmodified region. These 2'-modified "wings" further increase binding affinity and nuclease resistance while still allowing the center gap region to recruit RNase H. In some embodiments, the therapeutic DNA has a gamer design. It should be appreciated that the therapeutic DNA modifications, provided herein, are used as examples for the purposes of clarity and are not intended to be limiting.

Detecting RNA Interference (RNAi) Agents

Figure 4:
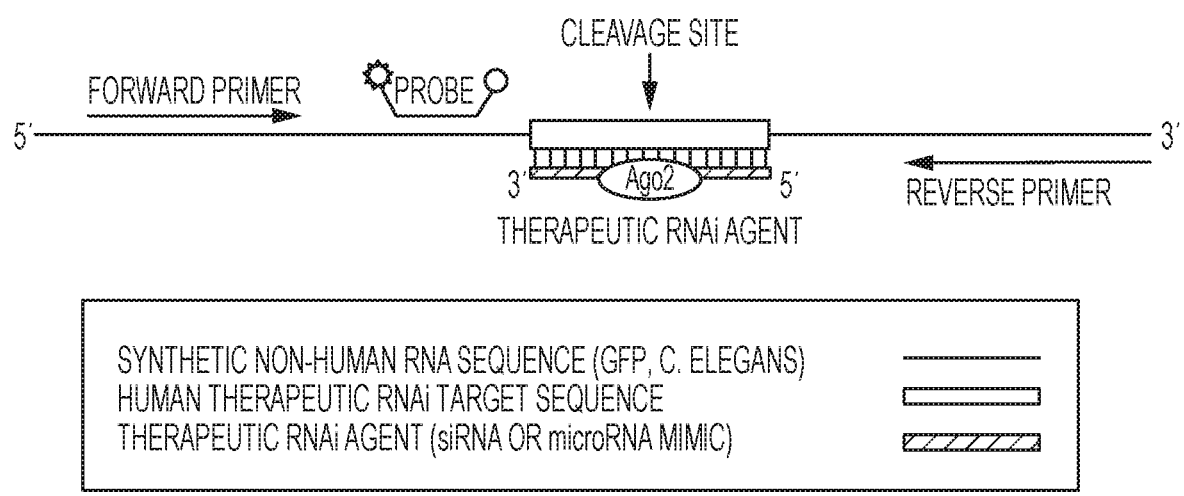
FIG. 4 shows a schematic of a non-limiting example of a synthetic ssRNA molecule bound to a single strand of an RNAi agent. In this non-limiting example, the therapeutic-binding region of the synthetic ssRNA is complementary to the RNAi agent. The synthetic ssRNA, when bound to the RNAi agent, is cleaved by an Argonaute protein of RNA-induced silencing complex (RISC) (indicated by the arrow). Also shown is a non-limiting example of a probe, such as a qPCR probe, which may have a fluorophore (shown as circle on the left side of the probe) and a quencher (shown as circle on the right side of the probe).
Figure 5:
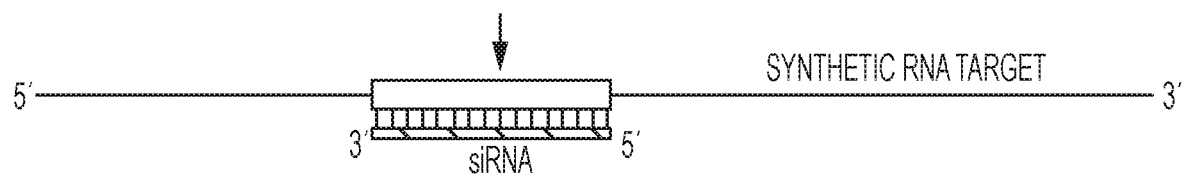
FIG. 5 shows a schematic of a non-limiting example of a synthetic ssRNA bound to a short-interfering RNA (siRNA) agent. The arrow indicates the site on the synthetic ssRNA that, when bound to the siRNA agent, may be cleaved by an Argonaute protein of RISC.

Aspects of the present disclosure are directed to methods of detecting, assessing the function of, and/or quantitating therapeutic RNA (e.g., RNAi agents) of interest. In some embodiments, the methods comprise (a) contacting a biological sample containing a therapeutic RNA with a synthetic single-stranded RNA (ssRNA) that is longer than (e.g., contains a flanking region on one or both sides of the region that is complementary to the therapeutic nucleic acid) and contains a region that is complementary to a nucleic acid strand of the therapeutic RNA, wherein the biological sample comprises an RNA-induced silencing complex containing an Argonaute protein, and (b) performing at least one assay to detect cleavage of the synthetic ssRNA. In the presence of a functional therapeutic RNA, the synthetic ssRNA and the therapeutic RNA bind to form an RNA-RNA duplex. This binding is guided by RNA-induced silencing complex (RISC). Non-limiting schematic representations of RNAi agents bound to a synthetic ssRNA are shown in FIG. 4 and FIG. 5.

RISC is a multiprotein complex that incorporates one strand of the therapeutic RNA (e.g., small interfering RNA (siRNA) or microRNA (miRNA)). RISC uses the RNA strand as a template for recognizing the complementary therapeutic-binding region of the synthetic ssRNA. When it finds the complementary therapeutic-binding region, RISC activates Argonaute (a protein within RISC) and cleaves the synthetic ssRNA. Detection of cleaved synthetic ssRNA is indicative of the presence of a functional therapeutic RNA in the sample, and detection of intact (e.g., uncleaved) synthetic ssRNA is indicative of the absence of a functional therapeutic RNA in the sample.

Argonaute proteins make up a highly conserved family whose members play a central role in RNA silencing processes as essential catalytic components of the RNA-induced silencing complex (RISC). Some non-limiting examples of Argonaute proteins include, but are not limited to, Ago-1, Ago-2, Ago-3, Ago-4, PIWIL1, PIWIL 2, PIWIL 3 or PIWIL 4. In some embodiments, the Argonaute protein is an Ago-like protein or a Piwi-like protein. Descriptions of Argonaute proteins, including Ago-like and Piwi-like proteins have been previously described and are discussed in Tolia N. H. et al. *Slicer and the Argonautes.* 3(1), 2007, p. 36-43, which is incorporated by reference herein.

In some embodiments, the components of RISC (including the Argonaute protein) are added to the sample (or reaction mixture) containing the therapeutic RNA. In some embodiments, the components of RISC (including the Argonaute protein) are endogenous to the sample (e.g., the biological sample) containing the therapeutic RNA.

In some embodiments, a therapeutic RNA is an RNA interference (RNAi) agent. Examples of RNAi agents include, without limitation, short-interfering RNA (siRNA), micro RNA (miRNA), short-hairpin (shRNA) and antagomirs. In some embodiments, the therapeutic RNA is a single-stranded guide RNA (gRNA), a trans-activating RNA (trRNA), a riboswitch, a ribozyme or an RNA-splicing factor. Other therapeutic RNAs are contemplated herein.

A "siRNA" is a short double-stranded RNA with a phosphorylated 5' end and a hydroxylated 3' end. In some embodiments, each end of a siRNA has an overhanging nucleotide. In some embodiments, each end of a siRNA has two overhanging nucleotides. A siRNA is produced, in some embodiments, from long, double-stranded RNAs or shRNAs via cleavage by a Dicer enzyme.

A "shRNA" is a single RNA strand that contains two complementary regions that hybridize to one another to form a double-stranded "stem" with the two complementary regions being connected by a single-stranded loop.

A "miRNA" is a small non-coding RNA molecule that forms short hairpins. A miRNA, in some embodiments, has less than perfect complementary regions that hybridize with each other to form a double-stranded stem connected by a single-stranded loop. A miRNA typically functions in RNA silencing and post-transcriptional regulation of gene expression. In some embodiments, a miRNA is endogenously produced, for example, in a eukaryotic cell.

An "antagomir" is a nucleic acid that prevents other molecules from binding to a desired site on an RNA molecule. In some embodiments, an antagomir is a synthetic nucleic acid. Typically, antagomirs have one or more modifications, such as 2'-methoxy groups and/or phosphorothioates, to render them more resistant to degradation. In some embodiments, an antagomir is complementary to a desired site on an RNA molecule. In some embodiments, an antagomir is perfectly complementary to a desired site on an RNA molecule. An antagomir, in some embodiments, is a miRNA inhibitor. A miRNA inhibitor, as used herein, is a single-stranded RNA which specifically binds a miRNA and inhibits miRNA function, for example, endogenous miRNA function. A miRNA inhibitor is, in some embodiments, used to silence endogenous miRNAs.

The length of a therapeutic RNA (e.g., RNAi agent) may vary. In some embodiments, the RNAi agent has a length of at least 5 nucleotides. In some embodiments, a therapeutic DNA has a length of at least 10 nucleotides, at least 15 nucleotides, at least 20 nucleotides, at least 25 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, or at least 500 nucleotides.

An RNAi agent, in some embodiments, has one or more modifications. Typically, modifications to an RNAi agent are made to enhance their stability or half-life, in vivo and/or in vitro. In some embodiments, an RNAi agent is a synthetic RNAi agent that includes modified nucleotides, such as those with chemical modifications to the 2'-OH group in the ribose sugar backbone, such as 2'-O-methyl (2'OMe), 2'-fluoro (2'F) substitutions, and those containing 2'OMe, or 2'F, or 2'-deoxy, or locked nucleic acid (LNA) modifications. Modifications to any of the RNAi agents, provided herein, are exemplary and are not intended to be limiting.

Detecting and Quantifying Cleaved Synthetic ssRNA

The methods, provided herein, further include performing at least one assay to detect cleavage of a synthetic ssRNA. When a synthetic ssRNA is bound to a nucleic acid (e.g., an ASO or an RNAi agent), the synthetic ssRNA is cleaved by an enzyme (e.g., RNase H or Ago2). Accordingly, the amount of cleaved synthetic ssRNA is indicative of the amount of therapeutic nucleic acid present in the reaction. Detection of cleaved synthetic ssRNA can be performed by any suitable method. In some embodiments, cleavage of the synthetic ssRNA is detected using an amplification reaction (e.g., PCR). For example, at least a portion of a reaction mixture containing a synthetic ssRNA, a therapeutic nucleic acid and an enzyme (e.g., RNase H or Ago2) may be subjected to a reverse transcription reaction using a primer that is complementary to and binds specifically to the synthetic ssRNA. The reverse transcription reaction produces complementary DNA (cDNA) from the synthetic ssRNA, which may be detected using PCR. In some embodiments, the methods further include performing a PCR reaction from cDNA generated in a reverse transcription reaction using primers that are complementary to and bind specifically to the cDNA. In some embodiments the primers are designed to specifically amplify cDNA generated from synthetic ssRNA that was not cleaved. Accordingly, the amount of synthetic ssRNA that was not cleaved can be quantified. In some embodiments, the cDNA generated from reverse transcribing the synthetic ssRNA is detected using quantitative PCR (qPCR). The qPCR process involves amplification of one or more specific sequences in a DNA sample using regular PCR techniques. The PCR products are quantified in real time using a probe (typically a fluorescent probe) that is included in the reaction mixture. The fluorescent probe, in some embodiments, emits signals based on the amount of the double-stranded DNA products to provide real-time quantification.

In some embodiments, cleavage of the synthetic ssRNA is detected using gel electrophoresis. For example, at least a portion of a reaction mixture containing a synthetic ssRNA, a therapeutic DNA, and an RNase H can be subjected to gel electrophoresis to determine the proportion of synthetic ssRNA that has been cleaved.

Also, provided herein, are methods of determining the amount of a therapeutic nucleic acid in a sample (e.g., a sample containing the therapeutic nucleic acid). In some embodiments, a blocker is added to the sample prior to adding a synthetic ssRNA to the sample. A "blocker" is an agent that binds a therapeutic nucleic acid and prevents the therapeutic nucleic acid from binding to a synthetic ssRNA. In some embodiments, a blocker is a nucleic acid, such as DNA or RNA. The purpose of a blocker, in some embodiments, is to prevent a therapeutic nucleic acid from binding to a synthetic ssRNA. A blocker may be titrated into a sample at known concentrations and the proportion of cleaved synthetic ssRNA can be determined in order to calculate the amount of therapeutic nucleic acid in the sample. In some embodiments, a blocker is used to calculate the half maximal inhibitory concentration ($IC_{50}$). An $IC_{50}$ is a quantitative measure that indicates how much of a particular substance (e.g., a blocker) is needed to inhibit a given biological process (e.g., binding of a therapeutic nucleic acid to a synthetic ssRNA) by half.

A blocker may have one or more of modifications, such as 2'-methoxy groups and/or phosphorothioates, to render the blocker more resistant to degradation and/or to render it amenable to binding therapeutic nucleic acids. It should be appreciated that modifications to any of the blockers, as provided herein, are exemplary and are not intended to be limiting.

In some embodiments, a blocker is complementary to a therapeutic nucleic acid. In some embodiments, a blocker is perfectly complementary to a therapeutic nucleic acid. A blocker, in some embodiments, is complementary to a DNA ASO. In some embodiments, a blocker is complementary to an RNAi agent. The length of a blocker may vary. In some embodiments, a blocker has a length of at least 5 nucleotides. In some embodiments, a blocker has a length of at least 10 nucleotides, at least 15 nucleotides, at least 20 nucleotides, at least 25 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 125 nucleotides, at least 150 nucleotides, at least 175 nucleotides, at least 200 nucleotides, at least 250 nucleotides, at least 300 nucleotides, at least 350 nucleotides, at least 400 nucleotides, at least 450 nucleotides, or at least 500 nucleotides.

Samples

Methods, as provided herein, may be used to detect a therapeutic nucleic acid present in a sample. A sample, in some embodiments, may be a non-biological sample or a biological sample. A "non-biological sample" refers generally to a sample that does not contain biological material (e.g., material from a subject or a cell). For example, a non-biological sample may be a buffer. In some embodiments the buffer comprises a therapeutic nucleic acid, which may be detected using a synthetic ssRNA of the present disclosure. In some embodiments, a sample is a biological sample. A "biological sample" refers to any biological material which may be obtained from a subject or cell. For example, a biological sample may be whole blood, plasma, serum, saliva, cerebrospinal fluid, urine, cells (or cell lysate) or tissue (e.g., normal tissue or tumor tissue). In some embodiments, a biological sample is a fluid sample.). In some embodiments, a biological sample is a biopsy sample. In some embodiments, a biological sample is a solid tissue, which may be made into a fluid sample using routine methods in the art.

A biological sample may also include one or more cells of a cell line. In some embodiments, a cell line includes human cells, primate cells (e.g., vero cells), rat cells (e.g., GH3 cells, OC23 cells) or mouse cells (e.g., MC3T3 cells). There are a variety of human cell lines, including, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells. Additional non-limiting examples of cell lines that may be used in accordance with the present disclosure include 293-T, 293-T, 3T3, 4T1, 721, 9L, A-549, A172, A20, A253, A2780, A2780ADR, A2780cis, A431, ALC, B16, B35, BCP-1, BEAS-2B, bEnd.3, BHK-21, BR 293, BxPC3, C2C12, C3H-10T1/2, C6, C6/36, Cal-27, CGR8, CHO, CML T1, CMT, COR-L23, COR-L23/5010, COR-L23/CPR, COR-L23/R23, COS-7, COV-434, CT26, D17, DH82, DU145, DuCaP, E14Tg2a, EL4, EM2, EM3, EMT6/AR1, EMT6/AR10.0, FM3, H1299, H69, HB54, HB55, HCA2, Hepalc1c7, High Five cells, HL-60, HMEC, HT-29, HUVEC, J558L cells, Jurkat, JY cells, K562 cells, KCL22, KG1, Ku812, KYO1, LNCap, Ma-Mel 1, 2, 3 . . . 48, MC-38, MCF-10A, MCF-7, MDA-MB-231, MDA-MB-435, MDA-MB-468, MDCK II, MG63, MONO-MAC 6, MOR/0.2R, MRCS, MTD-1A, MyEnd, NALM-1, NCI-H69/CPR, NCI-H69/LX10, NCI-H69/LX20, NCI-H69/LX4, NIH-3T3, NW-145, OPCN/OPCT Peer, PNT-1A/PNT 2, PTK2, Raji, RBL cells, RenCa, RIN-5F, RMA/RMAS, S2, Saos-2 cells, Sf21, Sf9, SiHa, SKBR3, SKOV-3, T-47D, T2, T84, THP1, U373, U87, U937, VCaP, WM39, WT-49, X63, YAC-1 and YAR cells.

In some embodiments, methods of the present disclosure involve obtaining a biological sample from a subject. As used herein, the phrase "obtaining a biological sample" refers to any process for directly or indirectly acquiring a biological sample from a subject. For example, a biological sample may be obtained (e.g., at a point-of-care facility, e.g., a physician's office, a hospital, laboratory facility) by procuring a tissue or fluid sample (e.g., blood draw, marrow sample, spinal tap) from a subject. Alternatively, a biological sample may be obtained by receiving the biological sample (e.g., at a laboratory facility) from one or more persons who procured the sample directly from the subject. A biological sample may be, for example, a fluid (e.g., blood), tissue, or cell (e.g., hematopoietic cell such as hematopoietic stem cell, leukocyte, or reticulocyte, stem cell, or plasma cell) sample obtained from the subject.

A "subject" may be any organism from which a sample (e.g., a biological sample) is obtained. Examples of subjects include, without limitation, animals (e.g., mammals such as humans, non-human primates, mice, rats and rabbits) and plants.

In some embodiments, a therapeutic nucleic acid is administered to a subject. Following administration of a therapeutic nucleic acid to a subject, a biological sample may be obtained from the subject to determine whether the therapeutic nucleic acid is present (and/or functional) in the biological sample. The therapeutic nucleic acids and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), and/or the condition of the subject (e.g., whether the subject is able to tolerate oral administration).

While therapeutic nucleic acids can be delivered exogenously to cells, intracellular synthesis of therapeutic nucleic acids may also be achieved by introducing a plasmid or vector containing a promoter operably linked to a template for transcription of the therapeutic nucleic acid into the cell, e.g., to create a stable cell line or transgenic organism.

Targets

The present disclosure also provides therapeutic biologically-active nucleic acids (e.g., antisense oligonucleotides and RNA interference (RNAi) agents) that alter the expression of target genes (e.g., therapeutic target genes). The nucleic acids of the present disclosure may alter the expression of any target gene (e.g., a target gene related to a disease or condition). Exemplary disease-related therapeutic target genes include, but are not limited to SOD1, C9ORF72 and DMPK. Additional non-limiting examples of target genes include genes that encode cytoskeletal proteins (e.g., actin, arp2/3, coronin, dystrophin, FtsZ, keratin, myosin, nebulin, spectrin, tau, titin, tropomyosin, tubulin and collagen) and extracellular matrix proteins (e.g., collagen, elastin, f-spondin, pikachurin, and fibronectin); globular proteins such as plasma proteins (e.g., serum amyloid P component and serum albumin), coagulation factors (e.g., complement proteins, C1-inhibitor and C3-convertase, Factor VIII, Factor XIII, fibrin, Protein C, Protein S, Protein Z, Protein Z-related protease inhibitor, thrombin, Von Willebrand Factor) and acute phase proteins such as C-reactive protein; hemoproteins; cell adhesion proteins (e.g., cadherin, ependymin, integrin, Ncam and selectin); transmembrane transport proteins (e.g., CFTR, glycophorin D and scramblase) such as ion channels (e.g., ligand-gated ion channels such nicotinic acetylcholine receptors and GABAa receptors, and voltage-gated ion channels such as potassium, calcium and sodium channels), synport/antiport proteins (e.g., glucose transporter); hormones and growth factors (e.g., epidermal growth factor (EGF), fibroblast growth factor (FGF), vascular endothelial growth factor (VEGF), peptide hormones such as insulin, insulin-like growth factor and oxytocin, and steroid hormones such as androgens, estrogens and progesterones); receptors such as transmembrane receptors (e.g., G-protein-coupled receptor, rhodopsin) and intracellular receptors (e.g., estrogen receptor); DNA-binding proteins (e.g., histones, protamines, CI protein); transcription regulators (e.g., c-myc, FOXP2, FOXP3, MyoD and P53); immune system proteins (e.g., immunoglobulins, major histocompatibility antigens and T cell receptors); nutrient storage/transport proteins (e.g., ferritin); chaperone proteins; and enzymes. Additional non-limiting examples of target genes can be found in the Therapeutic target database (Therapeutic target database update 2012: a resource for facilitating target-oriented drug discovery. Zhu F. et al. Nucleic Acids Res. 2012 January; 40 (Database issue): D1128-D1136; the contents of which are incorporated herein by reference).

Compositions

The present disclosure also provides compositions comprising a therapeutic DNA, a single-stranded synthetic ribonucleic acid (RNA) that is longer than and contains a region that is complementary to the therapeutic DNA, and RNase H. Further provided herein are compositions that comprise a therapeutic RNA, a synthetic single-stranded ribonucleic acid (ssRNA) that is longer than and contains a region that is complementary to the therapeutic RNA, and an RNA-induced silencing complex containing an Argonaute protein. The compositions of the present disclosure may further comprise a blocker, a buffer, a salt or an excipient.

Kits

The present disclosure also provides kits for detecting and/or quantifying nucleic acids (e.g., therapeutic nucleic acids) of interest. In some embodiments, the kits comprise a single-stranded synthetic ribonucleic acid (RNA) that is longer than and contains a region that is complementary to the therapeutic DNA and RNase H. In some embodiments, the kits comprise a synthetic single-stranded ribonucleic acid (ssRNA) that is longer than and contains a region that is complementary to the therapeutic RNA and an RNA-induced silencing complex containing an Argonaute protein. The kits of the present disclosure may further comprise a blocker, a buffer, a salt or an excipient.

EXAMPLES

Example 1

The present example describes experiments conducted to detect the presence of a DNA antisense oligonucleotide (ASO) using a synthetic ssRNA of the present disclosure. A schematic representation of a synthetic ssRNA molecule bound to a nucleotide target is shown in FIG. 1. Experiments were conducted to assess the ability of a synthetic RNA molecule to detect (a) varying concentrations of the DNA-based Malat1 ASO (TGCCTTTAGGATTCTAGACA, SEQ ID NO: 1, referred to herein as $MLT^{DNA}$) and (b) varying concentrations of the 2' O-Methyl-modified Malat1 ASO (UGCCTTTAGGATTCTAGACA, SEQ ID NO: 2, referred to herein as $MLT^{2'OMe}$. The first four nucleotides (UGCC) and the last four nucleotides (GACA) of SEQ ID NO: 2 are 2' O-Methyl-modified RNA bases. Nucleotides 5-16 of SEQ ID NO: 2 are DNA bases.

In the first experiment, the $MLT^{DNA}$ ASO (SEQ ID NO: 1) was titrated into a reaction at concentrations ranging from 100 fM to 100 nM in a 20 µl final reaction volume, containing 10 nM of a synthetic ssRNA molecule (GGAGUUGUCCCAAUUCUUGUUGAAUUAG AUGGUGAUGUCUAGAAUCCUAAAGGCACUGUCAGUG-GAGAGGGUGAAGGUGA UGCAACAUACG-GAAAACUUACCCUUAAA, SEQ ID NO: 3) having a region complementary to the Malat1 sequence and flanking forward and reverse primer sites. Nucleotides 10-35 of SEQ ID NO: 3 comprise the forward primer binding site, nucleotides 36-55 of SEQ ID NO: 3 are complementary to the Malat1 sequence, nucleotides 56-72 of SEQ ID NO: 3 include the probe binding site, and nucleotides 74-95 of SEQ ID NO: 3 include the reverse primer binding site.

Figure 2:
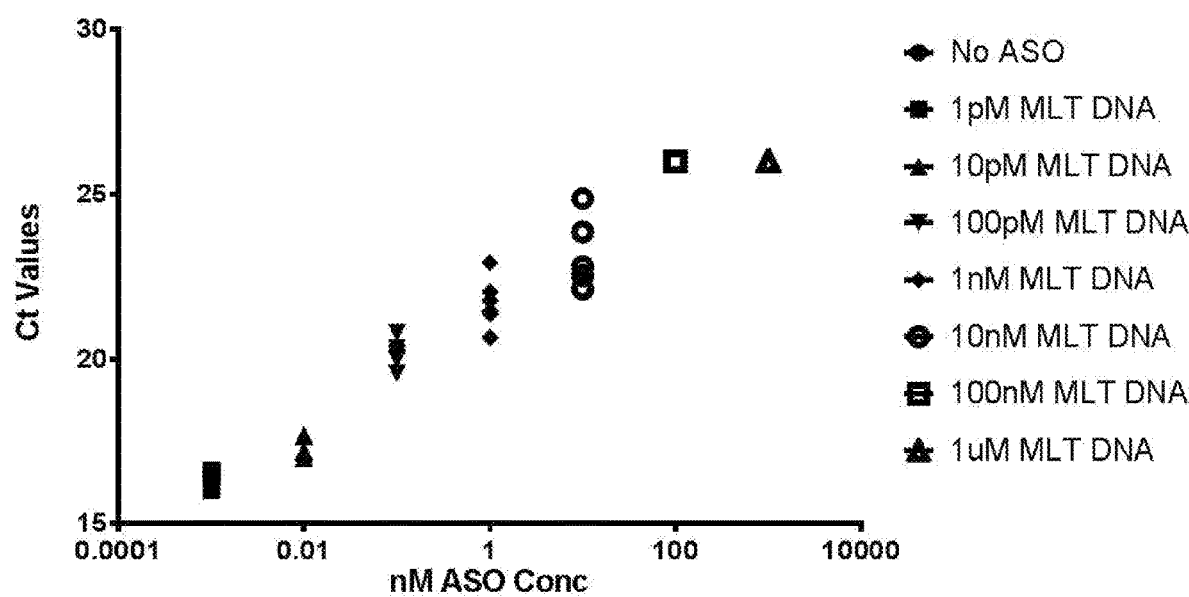
FIG. 2 shows a graph of threshold cycle ($C_t$) values for a quantitative polymerase chain reaction (PCR) containing 10 nM of synthetic RNA in response to increasing concentrations of a DNA ASO that binds to malat1.

The $MLT^{DNA}$ ASO and synthetic ssRNA molecule were incubated to allow binding before adding RNase H. The RNase H preferentially cleaves the synthetic ssRNA molecule that is bound to the MLT$^{DNA}$. The amount of intact synthetic ssRNA reflects the concentration of the MLT$^{DNA}$ in the reaction. The RNase H was heat inactivated and the reaction was subjected to a reverse transcription reaction. Amplification of the reverse transcript was performed by quantitative PCR (qPCR) run on Fluidigm, according to standard procedures. The standard procedures used were as follows: 1.25 μl of cDNA was added to the assay 1.25 μl (0.2×) and 2.5 μl of Taqman preamp master mix in a 5 μl reaction volume. 14 cycles of preamp were as follows: 10 min at 95C followed by 14 cycles of 95° C. for 15 seconds and 60° C. for 4 minutes. The reaction is then cooled to 4° C. qPCR was performed as described in the Fluidigm 96.96 Real-Time PCR workflow quick reference guide. A summary of the protocol used is shown in Table 1. Six threshold cycle values ($C_t$) for seven different concentrations of MLT$^{DNA}$, ranging from 100 fM to 100 nM in a 20 μl final reaction volume, were obtained and plotted (FIG. 2) to confirm assay function. The threshold cycle ($C_t$) is a relative measure of the concentration of target (e.g., the synthetic RNA molecule) in the PCR reaction. At low concentrations of MLT$^{DNA}$ (e.g., 1 pM), only a small portion of the synthetic RNA is cleaved. Accordingly, the concentration of in-tact synthetic ssRNA is higher, leading to a low $C_t$ value. The data (FIG. 2) show that as the concentration of MLT$^{DNA}$ increases, the $C_t$ value also increases since a greater proportion of the synthetic RNA molecule is cleaved. These experiments demonstrate the ability of the synthetic ssRNA molecules to detect a DNA antisense oligonucleotide.

TABLE 1

Summary of protocol used to determine the relative amount of synthetic RNA in the reaction following RNase H mediated cleavage.

| RNase Reaction | |
| --- | --- |
| Malat1 target (10 nM) | 1 μl |
| ASO | 2 μl Titration of ASO concentration |
| NEB RNase | 2 μl 5 U/μl |
| 10X buffer | 1 μl |
| water | 4 μl |
| Total Reaction volume | 10 μl |

Pre-incubate buffer oligo and target at 95 C. with slow cool to 30 C. using program 'Detect95D'
Add RNase H where appropriate and then follow 'DRDetect' for the RNase H reaction.
Incubate @ 37 C. for 60 minutes
Heat to 65 C. for 15 minutes to heat inactivate enzyme
Add the following with 5 minutes remaining in the 65 C. incubation:

| Reverse Transcriptase Reaction | |
| --- | --- |
| GSP (gene specific primers) | 1 μl (2 pmol each) |
| water | 1 μl |
| 10 mM dNTPs | 1 μl |
| Total Reaction Volume | 13 μl total reaction in tube |

Cool reaction to 4 C. for 5 minutes
Quick spin contents
Add the following:

| | |
| --- | --- |
| 5x First-Strand Buffer | 4 μl |
| 0.1M DTT | 1 μl |
| RNase inhibitor | 1 μl |
| Superscript | 1 μl (200 U/μl) |
| | 20 μl total reaction |

Incubate @ 25 C. for 5 minutes
Incubate @ 55 C. for 60 minutes
Heat inactivate at 70 C. for 15 minutes
Run on Fluidigm according to standard procedures.

Figure 3:
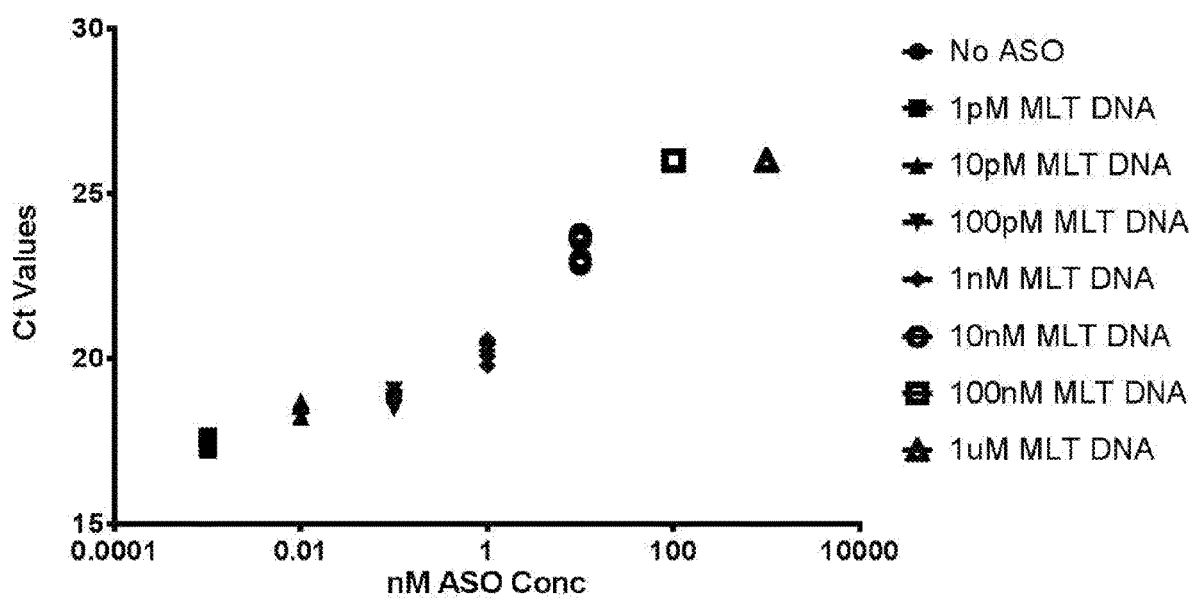
FIG. 3 shows a graph of threshold cycle ($C_t$) values for quantitative PCR reactions containing 10 nM of synthetic ssRNA in response to increasing concentrations of a 2' O-methyl-modified DNA ASO that binds to malat1 (MLT$^{2'OMe}$).

Further experiments were conducted to test whether the synthetic ssRNA molecule could detect MLT$^{2'OMe}$. 2' O-methyl (2'OMe) modifications are generally used in conjunction with DNA and are usually considered a solution for nuclease stability issues or the duplex stability of DNA molecules. The experiments were conducted as described above with MLT$^{DNA}$ (Table 1). Six threshold cycle values ($C_t$) for seven different concentrations of MLT$^{DNA}$, ranging from 1 pM to 1 μM, were obtained and plotted (FIG. 3) to confirm assay function. While, these data show that the synthetic ssRNA was able to detect 2'OMe modified DNA oligonucleotides comparably to DNA oligonucleotides, the results presented below further demonstrate that the synthetic ssRNA molecules of the present disclosure can also be used to detect RNA oligonucleotides.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of and" consisting essentially of shall be closed or semi-closed transitional phrases, respectively, as set forth in the United States Patent Office Manual of Patent Examining Procedures, Section 2111.03.

What is claimed is:

1. A method of detecting a therapeutic nucleic acid, the method comprising:
   (a) contacting a therapeutic nucleic acid with (i) a synthetic single-stranded ribonucleic acid (ssRNA) that is longer than and contains a region that is complementary to the therapeutic nucleic acid under conditions that permit nucleic acid hybridization, and (ii) an enzyme that binds to double-stranded nucleic acid and is capable of mediating cleavage of the synthetic ssRNA, thereby forming a first reaction mixture, wherein the therapeutic nucleic acid is obtained from or present in a biological sample that is from a human subject that has been administered the therapeutic nucleic acid, and wherein the ssRNA contains a non-human RNA sequence on one or both sides of the region that is complementary to the therapeutic nucleic acid; and (b) performing at least one assay to detect cleavage of the synthetic ssRNA, wherein cleavage of the synthetic ssRNA is indicative of the presence of the therapeutic nucleic acid in the human subject.

2. The method of claim 1, wherein the therapeutic nucleic acid is obtained from a biological sample, wherein the enzyme is endogenous in the biological sample.

3. The method of claim 1, wherein the therapeutic nucleic acid is a therapeutic deoxyribonucleic acid (DNA).

4. The method of claim 3, wherein the therapeutic nucleic acid is a single-stranded target DNA, optionally wherein the single-stranded target DNA is an antisense oligonucleotide (ASO).

5. The method of claim 1, wherein the enzyme is RNase H.

6. The method of claim 1, wherein step (b) comprises performing a reverse transcription reaction using at least a portion of the first reaction mixture and a primer that is complementary to and binds specifically to the synthetic ssRNA, thereby producing a second reaction mixture.

7. The method of claim 6, wherein step (b) further comprises performing a nucleic acid amplification reaction using at least a portion of the second reaction mixture and a pair of primers that are complementary to and bind specifically to a complementary DNA (cDNA) produced by the reverse transcription reaction, and wherein amplification of a nucleic acid indicates that the enzyme did not cleave the synthetic ssRNA.

8. The method of claim 7, wherein the nucleic acid amplification reaction is a quantitative polymerase chain reaction (qPCR).

9. The method of claim 1, wherein a blocker is added to the first reaction mixture for determining the level of the therapeutic nucleic acid.

10. The method of claim 1, wherein the therapeutic nucleic acid is a therapeutic DNA, and the enzyme is RNase H.

11. The method of claim 2, wherein the therapeutic nucleic acid is a therapeutic ribonucleic acid (RNA), and wherein the biological sample comprises an RNA-induced silencing complex containing an Argonaute protein.

12. The method of claim 11, wherein the biological sample is obtained from a subject, optionally wherein the therapeutic RNA is administered to the subject.

13. The method of claim 12, wherein the therapeutic RNA is an RNA interference (RNAi) agent selected from the group consisting of: a short-hairpin RNA (shRNA), short-interfering RNA (siRNA), a micro RNA (miRNA) and a miRNA inhibitor, optionally wherein the RNA-induced silencing complex is endogenous in the biological sample.

14. The method of claim 11, wherein step (b) comprises performing a reverse transcription reaction using at least a portion of the first reaction mixture and a primer that is complementary to and binds specifically to the synthetic ssRNA, thereby producing a second reaction mixture.

15. The method of claim 14, wherein step (b) further comprises performing a nucleic acid amplification reaction using at least a portion of the second reaction mixture and a pair of primers that are complementary to and bind specifically to a complementary DNA (cDNA) produced by the reverse transcription reaction, and wherein amplification of a nucleic acid indicates that the Argonaute protein did not cleave the synthetic ssRNA.

16. The method of claim 15, wherein the nucleic acid amplification reaction is a quantitative polymerase chain reaction (qPCR).

17. The method of claim 11, wherein a blocker is added to the biological sample for determining the level of the therapeutic RNA.

18. The method of claim 1, wherein the biological sample comprises
whole blood, plasma, serum, saliva, cerebrospinal fluid, urine, cells, or tissue.

19. The method of claim 1, wherein the biological sample comprises cell lysate.

* * * * *